United States Patent [19]

Fuchs et al.

[11] Patent Number: 5,380,896
[45] Date of Patent: Jan. 10, 1995

[54] PROCESS FOR THE PREPARATION OF DIORGANOTIN MERCAPTOCARBOXYLATES

[75] Inventors: Reiner Fuchs, Ober-Ramstadt; Johannes Kaufhold; Kornelia Malzacher, both of Lindenfels, all of Germany

[73] Assignee: Ciba-Geigy Corporation, Ardsley, N.Y.

[21] Appl. No.: 82,184

[22] Filed: Jun. 24, 1993

[30] Foreign Application Priority Data

Jun. 30, 1992 [CH] Switzerland ............... 2040/92-0

[51] Int. Cl.⁶ .............................................. C07F 7/22
[52] U.S. Cl. .................................................. 556/91
[58] Field of Search ........................................ 556/91

[56] References Cited

U.S. PATENT DOCUMENTS 3,349,109 10/1967 Lach .................... 260/429.7
5,238,605 8/1993 Abeler et al. ............ 252/400.1

FOREIGN PATENT DOCUMENTS 0446174 9/1991 European Pat. Off.
449000 4/1968 Switzerland.
719733 12/1954 United Kingdom.
1055995 1/1967 United Kingdom.
1430933 4/1976 United Kingdom.

OTHER PUBLICATIONS

Derwent 65300v/37 (1972).
C.A. 85(11) 78202s (1991).
C.A. 115(9) 92614x (1991).
Derwent 69378y/39 (1975).
Derwent WPI Acc No: 91-269009/37 (1993).
C.A. 37348u vol. 75, 1971.

*Primary Examiner*—José G. Dees
*Assistant Examiner*—Porfirio Nazario-Gonzalez
*Attorney, Agent, or Firm*—Michele A. Kovaleski

[57] ABSTRACT

The invention relates to a process for the preparation of a pulverulent diorganotin mercaptocarboxylate, which comprises reacting a diorganotin oxide of the formula I,

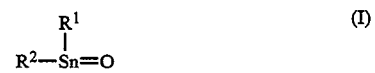

in which $R^1$ and $R^2$, independently of one another, are $C_1$–$C_{18}$alkyl, at a temperature in the range from 35° C. to 70° C. in the absence of solvents and/or adsorbents with a mercaptocarboxylic acid of the formula II

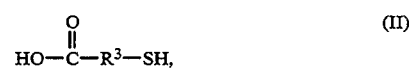

in which $R^3$ is alkylene having 1 to 18 C atoms or is phenylene, and subjecting the reaction mixture and product during the reaction and the subsequent cooling phase to constant thorough mixing.

The process products are suitable for the stabilisation of chlorine-containing polymers against the damaging effect of light, oxygen and/or heat.

15 Claims, No Drawings

PROCESS FOR THE PREPARATION OF DIORGANOTIN MERCAPTOCARBOXYLATES

The invention relates to a process for the preparation of pulverulent diorganotin mercaptocarboxylates.

The preparation of diorganotin mercaptocarboxylates from mercaptopropionic acid or esters thereof and diorganotin oxides or diorganotin chlorides in the presence of solvents is known; cf., for example, GB-A 1 430 933, DD-A 289 274 and JP-A 50/112 323.

DD-A 240 747 and DD-A 207 723 describe the addition of catalysts and drying agents for accelerating the reaction of mercaptocarboxylic esters with diorganotin oxides.

The use of auxiliaries creates difficulties in the preparation of the end product in pure film. In order to avoid them and at the same time to obtain a reaction rate which is still sufficiently high, the preparation was carried out at temperatures above 100° C. from the melt (JP-A 49/51227). However, the high reaction temperature in this process is unfavourable in terms of process engineering and economy; moreover, the products thus obtained are difficult to crystallise and retain a certain tackiness.

To accelerate crystallisation, the addition of catalysts, for example of small amounts of unreacted mercaptopropionic acid, was again proposed (JP-A 50/112 323).

EP-A 446 174 teaches a solvent-free preparation process for PVC stabilisers containing diorganotin mercaptocarboxylates in which adsorbents are added to the reaction mixture.

It has now been found that diorganotin oxides can surprisingly be reacted very rapidly with mercaptocarboxylates without using solvents or adsorbents to give pulverulent diorganotin mercaptocarboxylates by not exceeding in the reaction a maximum temperature of 70° C. and cooling the resulting product with constant thorough mixing. Accordingly, the invention relates to a process for the preparation of a pulverulent diorganotin mercaptocarboxylate, which comprises reacting a diorganotin oxide of the formula I,

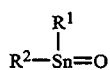

in which $R^1$ and $R^2$, independently of one another, are $C_1$–$C_8$alkyl, at a temperature in the range from 35° C. to 70° C. in the absence of solvents and adsorbents with a mercaptocarboxylic acid of the formula II

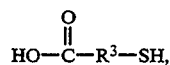

in which $R^3$ is alkylene having 1 to 18 C atoms or is phenylene, and subjecting the reaction mixture and product during the reaction and the subsequent cooling phase to constant thorough mixing.

Apart from the dialkyltin oxides mentioned, those compounds of the formula I in which $R^1$ and/or $R^2$ are $C_5$–$C_8$cycloalkyl, for example cyclopentyl, can also be used.

Preferably, the reaction mixture is constantly thoroughly mixed during the reaction and the cooling phase down to 30° C.

The product of the process according to the invention is a free-flowing solid. Depending on the composition and process conditions, the particle size of the product can vary to a large extent, for example between a few micrometers and several millimeters, ranging, example, from 5 μm to 5 mm, in particular ranging from 50 μm to 1 mm.

In the process according to the invention, the water of reaction formed is advantageously, removed at reduced pressure, for example at 50 to 300 hPa (=mbar).

The composition of the diorganotin oxides,is that of the formula I. Apart from monomers. oligomers, polymers or three-dimensional crystal lattices are also discussed as possible structures for these compounds; as to the constitution of these compounds, cf., for example, Houben-Weyl, Methoden der Organischen Chemie [Methods of Organic Chemistry], Vol. 13/6, p. 304, Thieme-Verlag, Stuttgart 1978. Hereinafter, diorganotin oxides are designated as compounds of the formula I regardless of possible deviating structures.

The diorganotin mercaptocarboxylates formed in the reaction of diorganotin oxide with mercaptocarboxylic acid in a molar ratio of 1:1 can be present as monomers of the formula III

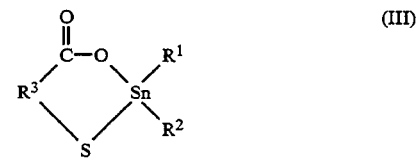

or as oligomers or polymers composed of recurring units of the formula IV

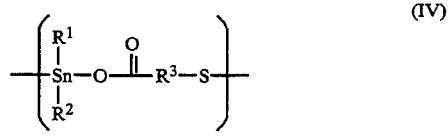

(R. Gächter, H. Müller, Plastics Additives Handbook, 3rd Ed., p. 282, Hanser-Verlag, Müinchen 1990; Houben-Weyl, Methoden der Organischen Chemie [Methods of Organic Chemistry, Vol. 13/6, p. 440–441, Thieme-Verlag, Stuttgart 1978).

The invention also relates to a process in which a mixture of various diorganotin oxides and/or mercaptocarboxylic acids is used instead of a uniform starting material of the formula I and a uniform starting material of the formula II and accordingly a mixture of various diorganotin mercaptocarboxylates is obtained.

The process according to the invention can lead to individual compounds or else to mixtures of products.

In the process according to the invention, the starting materials can be in equivalent amounts or else in almost equivalent amounts (molar ratio of diorganotin oxide to mercaptocarboxylic acid 0.9:1 to 1.1:1 ). It is also possible to use a fairly large excess of the diorganotin oxide of the formula I. Preferably, diorganotin oxide and mercaptocarboxylic acid are used in a molar ratio of 0.9:1 to 2.1: 1. Particular preference is given to a process in which the molar ratio is about 1:1, i.e. the organotin compound is employed in 0.95 to 1.05 times the equivalent amount, relative to the mercaptocarboxylic acid.

In the case where the diorganotin oxide is used in excess, the product also contains units of formula V

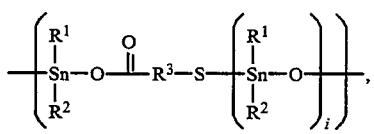

in which i is a number greater than 0, for example from the range 1 to 50.

In the case where less than an equivalent mount of diorganotin oxide is used, the product contains compounds in which only the carboxyl or the mercapto group of the mercaptocarboxylic acid is esterified with the tin compound.

Examples of $R^1$ and $R^2$ as $C_1$-$C_{18}$alkyl are methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl or octadecyl, in particular $C_1$-$C_{12}$alkyl, for example n-butyl or n-octyl.

Preferably, $R^1$ and $R^2$ are identical.

Particularly preferred diorganotin oxides are dibutyltin oxide, dioctyltin oxide and dilauryltin oxide.

Examples of preferred reactants of diorganotin oxide are thioglycolic acid, β-mercaptopropionic acid and thiosalicylic acid

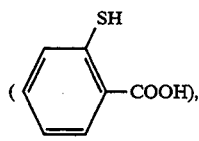

in particular β-mercaptopropionic acid.

In the process according to the invention, a diorganotin oxide of the formula I in which $R^1$ and $R^2$, independently of one another, are $C_4$-$C_2$alkyl is preferably used. Particularly preferably, $R^1$ and $R^2$, independently of one another, are butyl or octyl.

The mercaptocarboxylic acid used in the process according to the invention is preferably one of the formula IIa

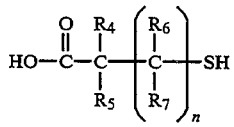

or of the formula IIb

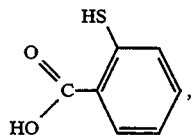

in which n is 0 or 1 and $R^4$, $R^5$, $R^6$ and $R^7$, independently of one another, are —H or $C_1$-$C_4$alkyl.

Particular preference is given to a process in which a mercaptocarboxylic acid of the formula IIa in which $R^4$, $R^5$, $R^6$ and $R^7$ be hydrogen or of the formula IIb is used.

Of very particular importance is a process wherein dibutyltin oxide or dioctyltin oxide is reacted with β-mercaptopropionic acid.

The process according to the invention is advantageously carried out in the absence of catalysts, in particular in the absence of drying agents or substances which increase the rate of the reaction and/or of the crystallisation of the product but do not have a stabilising function in chlorine-containing polymer compositions.

Particular preference is given to a process in which, apart from the starting materials of the formula I and of the formula II, no further compounds, auxiliaries or additives are used.

The process can be carried out, for example, in such a manner that the starting materials are premixed and then poured into the reactor; or the starting materials are introduced into the reactor in succession and then mixed and heated, it being possible, for example, to introduce a solid component as the initial charge and to add a liquid component by spraying while mixing the resulting reaction mixture. It is also possible to operate the process continuously by introducing the starting materials continuously in suitable amounts into the reaction zone of a suitable apparatus and discharging the finished product after cooling. The requirement is that constant thorough mixing is ensured.

Suitable apparatuses for carrying out the process are in principle all those which are capable of fulfilling the requirements mentioned with respect to temperature control, thorough mixing and, if desired, reduction in pressure. Advantageously, apparatuses which operate continuously are used; of these, not only those apparatuses exhibiting uniform residence time behaviour but also those typically leading to spreading of the residence time can be used, for example, heatable mixers, driers or extruders can serve as reaction apparatuses.

Examples of mixers are forced-type mixers, V-shaped mixers, Eirich-type mixers, ploughshare mixers, plough blade mixers, paddle mixers, mixing screws, vertical screw mixers or continuous mixers. Mixers which can be evacuated are particularly preferred.

The reaction is preferably carried out in driers which advantageously can also be evacuated. Driers of this type are known per se and can be, for example, kneading driers, paddle driers, trough driers, screw driers or vacuum disc driers.

As already described above, the individual components are advantageously introduced into the reaction vessel, then into the mixing device or the drying equipment in a manner appropriate to the device used. Liquid components are advantageously sprayed onto the solid component(s) by means of suitable devices.

After sufficient thorough mixing, the components are brought to the desired temperature; or, alternatively, a further component is metered to an already temperature-controlled component or mixture with sufficient thorough mixing.

The reaction of the starting materials takes place in the temperature range 35°-70° C., preferably in the temperature range 45°-65° C., in particular in the temperature range 5520 -65° C.

The reaction mixture is advantageously maintained at tile maximum temperature selected for not more than 2 hours, preferably for not more than 60 minutes. Within this period, the reaction goes to completion. The reaction times reached are, for example, 2 to 120 minutes, in particular 5 to 60 minutes, especially 5 to 30 minutes.

The water formed as a by-product of tile reaction is advantageously removed during this period and/or at the beginning of the cooling phase which follows. This can take place at atmospheric pressure or at reduced pressure, it being possible for the water to be collected within the apparatus by condensation or to be discharged in the form of vapour. It is preferred to apply vacuum. This vacuum is, for example, in the range from 1 to 500, preferably 10 to 500, in particular 50 to 300, especially 50 to 200 mbar.

After the reaction, the reaction mixture is cooled, preferably down to 30° C. or below that temperature, with further constant thorough mixing.

Thorough mixing and cooling rate are advantageously adjusted to one another such that at no time lumps or crusts are formed on built-in parts or walls of the apparatus; advantageously, each volume portion of the mixture which is larger than the particle size of the end product comes constantly into contact with other volume portions as a result of thorough mixing.

The diorganotin mercaptocarboxylates obtained by the process according to the invention can be used for the stabilisation of chlorine-containing polymers against the damaging effect of light, oxygen and/or heat. They are suitable, for example, for the following types of polymers: vinyl chloride polymers, vinylic resins having vinyl chloride units in their structure, such as copolymers of vinyl chloride and vinylesters of aliphatic acids, in particular vinyl acetate, copolymers of vinyl chloride with acrylic and methacrylic esters and with acrylonitrile, copolymers of vinyl chloride with diene compounds and unsaturated dicarboxylic acids or anhydrides thereof, such as copolymers of vinyl chloride with diethyl maleate, diethyl fumarate or maleic anhydride, post chlorinated polymers and copolymers of vinyl chloride, copolymers of vinyl chloride and vinylidene chloride with unsaturated aldehydes, ketones and others, such as acrolein, crotonaldehyde, vinyl methyl ketone, vinyl methyl ether, vinyl isobutyl ether and the like; polymers of vinylidene chloride and copolymers thereof with vinyl chloride and other polymerisable compounds; polymers of vinyl chloroacetate and dichlorodivinyl ether; chlorinated polymers of vinyl acetate, chlorinated polymeric esters of acrylic acid and alpha-substituted acrylic acid: polymers of chlorinated styrenes, for example dichlorosytrene; chlorinated rubbers; chlorinated ethylene polymers; polymers and post chlorinated polymers of chlorobutadiene and copolymers thereof with vinyl chloride, rubber hydrochloride and chlorinated rubber hydrochloride; and mixtures of the polymers mentioned with one another or with other polymerisable compounds.

Also included are graft polymers of PVC with EVA, ABS and MBS. Preferred substrates are also mixtures of the abovementioned homo- and copolymers, in particular vinyl chloride homopolymers, with other thermoplastic and/or elastomeric polymers, in particular blends with ABS, MBS, NBR, SAN, EVA, CPE, MBAS, PMA, PMMA, EPDM, polylactones and nitrile rubber.

Furthermore, suspension polymers, bulk polymers, and emulsion polymers are preferred.

A particularly preferred chlorine-containing polymer is polyvinyl chloride, in particular suspension polymers, emulsion polymers and bulk polymers.

Moreover, the process products can be used for further known applications of diorganotin mercaptocarboxylates; an example is the use as medicament for rumour control according to EP-A 472,783.

The solvent-free process according to the invention has, for example, the advantages that there is no need for removal, disposal and reprocessing of solvents, that it is free of adsorbents which may have an adverse effect on the use properties of the stabilised chlorine-containing polymer compositions and that the product can be used without any further processing as stabiliser in the form of a free-flowing solid.

The examples which follow further illustrate the process according to the invention. All parts and percentages given are by weight unless stated otherwise.

EXAMPLE 1

Preparation of Dioctyltin β-mercaptopropionate

In a kneading drier, 4.27 kg of β-mercaptopropionic acid are added by spraying to 14.53 kg of dioctyltin oxide over a period of 6 minutes. The mixture thus obtained is heated at 60° C. for a period of 20 minutes with thorough mixing and under a pressure of 120 hPa (=120 mbar), during which the water of reaction formed escapes. The mixture is then cooled to room temperature while thorough mixing of the product is continued. Dioctyltin β-mercaptopropionate is obtained as a white free-flowing solid.

Analysis $C_{19}H_{38}O_3S$ Sn: calc. 6.9 % S, 25.5 % Sn; found 6.0 % S, 25.3 % Sn; IR vibration at 1531 cm$^{-1}$; chemical shift in $^{119}$Sn NMR at +94 ppm.

EXAMPLE 2

Static Heating Test of Stabilised PVC 100.0 parts by weight of S-PVC (K value 60), 0.2 part by weight of monomic ester, 1.0 part by weight of glycerol monooleate and 1.6 parts by weight of dioctyltin β-mercaptopropionate (product from Example 1) are plasticised on mixing rolls at 190° C. for 5 minutes. Test specimens are punched out from the sheet thus obtained (thickness 0.2 mm) and subjected to thermal stress in a Mathis Thermo-Takter ® at 190° C. for the length of time given in Table 1. The Yellowness Index (YI) is then determined by ASTM D 1925-70. The results as listed in Table 1. The test documents the stabilising effect of the products of the process according to the invention.

TABLE 1

| Yellowness Index of the test specimens after exposure to stress at 190° C. | | | | | | |
| --- | --- | --- | --- | --- | --- | --- |
| Length of time (min): | 0 | 10 | 20 | 30 | 40 | 50 |
| YI: | 4.8 | 5.5 | 7.0 | 9.0 | 13.1 | 20.2 |

EXAMPLE 3

Preparation of dibutyltin β-mercaptopropionate

A mixture of 2.475 kg (23.3 tool) of 3-mercaptopropionic acid and 5.97 kg (24 mol) of dibutyltin oxide is continuously fed into a screw drier whose heat exchange areas consist of two heating and one cooling zone. Behind each heating zone, a suction device is present for removing the water of reaction formed.

The reaction mixture passes through both heating zones at an average residence time of 7.5 minutes, the temperature of the first heating zone being 68° C. and that of the second being 63° C., and is then cooled to 25°-30° C.

At the exit of the screw drier, dibutyltin 3-mercaptopropionate is obtained as a white free-flowing powder; its purity determined by IR spectroscopy is 95 %. Moreover, the end product contains 3-mercaptopropionates having Sn—O—Sn bonds in accordance with formula V (IR absorption at 490 cm$^{-1}$).

What is claimed is:

1. A process for the preparation of a pulverulent diorganotin mercaptocarboxylate, which comprises reacting a diorganotin oxide of the formula I

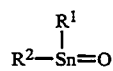 (I)

in which $R^1$ and $R^2$, independently of one another, are $C_1$–$C_{18}$alkyl, at a temperature in the range from 35° C. to 70° C. in the absence of solvents and adsorbents with a mercaptocarboxylic acid of the formula II

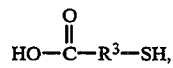 (II)

in which $R^3$ is alkylene having 1 to 18 C atoms or is phenylene, and subjecting the reaction mixture and product during the reaction and the subsequent cooling phase to constant thorough mixing.

2. A process according to claim 1, wherein a diorganotin oxide of the formula I is used in which $R^1$ and $R^2$, independently of one another, are $C_4$–$C_{12}$alkyl.

3. A process according to claim 1, wherein a diorganotin oxide of the formula I is used in which $R^1$ and $R^2$, independently of one another, are butyl or octyl.

4. A process according to claim 1, wherein a mercaptocarboxylic acid of the formula IIa

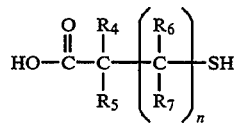 (IIa)

or of the formula IIb

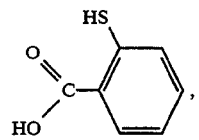 (IIb)

in which n is 0 or 1 and $R^4$, $R^5$, $R^6$ and $R^7$, independently of one another, are —H or $C_1$–$C_4$alkyl, is used.

5. A process according to claim 4, wherein a mercaptocarboxylic acid of the formula IIa in which $R^4$, $R^5$, $R^6$ and $R^7$ are hydrogen or of the formula IIb is used.

6. A process according to claim 1, wherein dibutyltin oxide or dioctyltin oxide is reacted with β-mercaptopropionic acid.

7. A process according to claim 1, wherein the reaction mixture is subjected during the reaction and the cooling phase down to 30° C. to constant thorough mixing.

8. A process according to claim 1, wherein the reaction is carried out in a temperature range of 45°–65° C.

9. A process according to claim 8, wherein the reaction is carried out in a temperature range of 55°–65° C.

10. A process according to claim 7, wherein the reaction does not exceed 60 minutes.

11. A process according to claim 1, wherein the water of reaction formed is removed at reduced pressure in the range from 50 to 300 hPa (=mbar).

12. A process according to claim 1, wherein the organotin compound is used in 0.9 to 2.1 times the equivalent amount, relative to the mercaptocarboxylic acid.

13. A process according to claim 12, wherein the organotin compound is used in 0.95 to 1.05 times the equivalent amount, relative to the mercaptocarboxylic acid.

14. A process according to claim 1, which is carried out in the absence of catalysts.

15. A process according to claim 1, wherein apart from the starting materials of formula I and formula II, no further compounds, auxiliaries or additives are used.

* * * * *